United States Patent [19]
Gonick et al.

[11] Patent Number: 4,962,127
[45] Date of Patent: Oct. 9, 1990

[54] METHOD FOR SILICON REDUCTION WITH DIMERCAPTOSUCCINIC ACID (DMSA)

[75] Inventors: Harvey C. Gonick; Farhad Khalil-Manesh, both of Los Angeles; Elmar W. J. Weiler, Inglewood, all of Calif.

[73] Assignee: Cedars-Sinai Medical Center, Los Angeles, Calif.

[21] Appl. No.: 325,297

[22] Filed: Mar. 17, 1989

[51] Int. Cl.$^5$ ............................................. A61U 31/185
[52] U.S. Cl. ........................................................ 514/578
[58] Field of Search ........................................... 514/578

[56] References Cited

PUBLICATIONS

Liang Yu-i et al., Studies on Antibilharzial Drugs VI, the Anti-dotal Effects of Sodium Dimercaptosuccinate and Bal-Glucoside Against Tartar Emetic, pp. 25–32.
J. L. Domingo et al., Development Toxicity of Subcutaneously Administered meso-2, 3-Dimercaptosuccinic Acid in Mice, Fund. Appl. Tox 11:715–722 (1988).
H. Vasken Aposhian, DMSA and DMPS-Water Soluble Antidotes for Heavy Metal Poisoning, Ann. Rev. Pharmacol. Toxicol. 23:193–215 (1983).
Deborah A. Cory-Slechta, Mobilization of Lead Over the Course of DMSA Chelation Therapy and Long-Term Efficacy, J. Pharm. Exp. Therap. 246:84 (1988).
Liang et al., Acta Physiol. Sin. 21:24–32 (1957).
Richard M. Maiorino et al., Determination and Metabolism of Dithiol–Chelating Agents: Electrolytic and Chemical Reduction of Oxidized Dithiols in Urine, Anal. Biochem. 160:217–226 (1987).
Jose L. Domingo et al., Acute Aluminum Intoxication: A Study of the Efficacy of Several Antidotal Treatments in Mice, Res. Com. Chem. Pathol. Pharm. 53:93–104 (1986).
Juan M. Llobet et al., Comparison of the Effectiveness of Several Chelators After Single Administration on the Toxicity, Excretion and Distribution of Cobalt, Arch. Toxicol. 58:278–281 (1986).
Louis R. Cantilena, Jr. et al., The Effect of Repeated Administration of Several Chelators on the Distribution and Excretion of Cadmium, Tox. Appl. Pharm. 66:361–367 (1982).
Juan M. Llobet et al., Antidotes for Zinc Intoxication in Mice, Arch. Toxicol. 61:321–323 (1988).
Hirsch Handmaker et al., Clinical Experience with $^{99m}$Tc–DMSA (Dimercaptosuccinic Acid), a New Renal-Imaging Agent, J. Nucl. Med., 16:28–32 (1973).
J. C. Watkinson et al., An Evaluation of the Uptake of Technetium-99m (V) Dimercaptosuccinic Acid in Patients with Squamous Carcinoma of the Head and Neck, Clin. Otalary 12:405–411 (1987).
C. A. Hoefnagel, M.D. et al., New Radionuclide Tracers for the Diagnosis and Therapy of Medullary Thyroid Carcinoma, Clin. Nucl. Med. 13:159–165 (1988).
Kenneth P. Lyons, M.D. et al., Myocardial Infarct Imaging in Patients with Technetium-99m 2, 3 Dimercaptosuccinic Acid Superiority of Technetium-99m Pyrophosphate, Clin. Nucl. Med. 12:514–518 (1987).

Primary Examiner—Stanley J. Friedman
Attorney, Agent, or Firm—Lyon and Lyon

[57] ABSTRACT

A method for silicon reduction with Dimercatosuccinic Acid (DMSA) is described. DMSA is administered to reduce levels of silicon in blood and tissue thereby reducing blood pressure, improving kidney function, preventing or retarding the progression of chronic renal failure, treating the accumulation of silicon in advanced kidney disease, and/or preventing the onset or improving the current status of dementia and Alzheimer's Disease.

14 Claims, 2 Drawing Sheets

METHOD FOR SILICON REDUCTION WITH DIMERCAPTOSUCCINIC ACID (DMSA)

FIELD OF THE INVENTION

This invention relates generally to a method for reduction of silicon levels with Dimercaptosuccinic Acid (DMSA). More particularly, this invention relates to a method for reduction of silicon levels in human blood and tissue with DMSA, in order to reduce blood pressure, improve kidney function, prevent or retard the progression of chronic renal failure, treat the accumulation of silicon in advanced kidney disease, and/or prevent the onset, or improve the current status of dementia and Alzheimer's Disease.

BACKGROUND OF THE INVENTION

Silicon, next to oxygen, is the most prevalent element on earth, and is the most abundant mineral in the earth's crust. It occurs in nature as silica oxides ($SiO_2$) or corresponding silicic acids. Silicon is present in plants, and is widespread in foodstuffs, particularly monocotyledons such as grain, in clay (aluminum silicate), in sand, and in glass. In medicine, silicon is used therapeutically as magnesium trisilicate, and as organic compounds used as defoaming agents. Silicones are used in various cosmetic surgical implant procedures. Due most probably to dietary intake, at least small amounts of silicon may be found in most animal tissues and fluids (*Scot Med J.* 27:17-19 (1982)).

Silicon is a trace element, comprising less than 0.01% of the human body. Silicon has been demonstrated as an essential element, i.e. one that is required for maintenance of life, and when deficient, consistently results in an impairment of a function from optimal to suboptimal (*Science* 213:1332 (1981)).

Proof of the essentiality of silicon was independently established by two investigators. Carlisle established a silicon deficiency state incompatible with normal growth in chicks (*Science* 178:619 (1972)), and Schwartz and Milne showed similar results with rats (*Nature,* 239:33 (1972)). Using comparable methods, both studies showed that the animals responded to supplementation with sodium metasilicate with a 30 to 50 percent stimulation in growth. Subsequent examination of the animals raised on silicon-deficient diets revealed depressed bone growth and severe bone deformaties, particularly of the skull.

Although silicon has been known as a regular constituent of biological materials since the beginning of the century, little is known about its metabolism. It is known that silicon specifically concentrates in the mitochondria of osteoblasts, and that it plays a role in bone and cartilage formation (*Science* 213:1332 (1981)). In addition, since silicon is present in high concentrations in collagen, it has been suggested that silicon plays a role in cross-linking connective tissues at the level of mucopolysaccharides (*Fed. Proc.* 33:1748 (1974)). It has therefore been postulated that apart from bone formation, silicon participates in growth and maintenance of connective tissue, as in embryonic development and wound healing and in regulation of ions, metabolites and water in connective tissue. (*Fed. Proc.* 33:1758-1766 (1974)).

Silica in foods and beverages is readily absorbed across the intestinal wall. Studies have shown that there is a narrow range of silicon concentration in the serum of healthy adults, and with the exception of urine, the concentrations of silicon in all other body fluids is similar to that of normal serum. Higher and wider rangers of silicon levels in the urine show that the kidney is the main excretory organ for silicon absorbed from the alimentary canal (*Scot Med J.* 27:17-19 (1982)).

The level of silicon in the blood and tissues has been shown to be affected by age, as well as sex, castration, adrenalectomy and thyroidectomy (*Ann endocrinol* 32:397 (1971)). The silicon content of the aorta, skin and thymus in the rabbit, rat, chicken and pig was found to significantly decline with age, whereas other tissues such as the heart, kidney, muscle and tendon show little or no change (*Fed. Proc.* 33:1758-1766 (1974)). In addition, the silicon content of the dermis of human skin has been shown to diminish with age (*J. Biol. Chem.* 75:789-794 (1927)). In contrast, Leslie et al. showed an increase in rat brain, liver, spleen, lung and femur silicon with age (*Proc. Soc. Exptl. Bio. Med.* 110:218 (1962)). And Kworning et al. described elevated silicon deposition in the human aorta wall during aging (*J. Geront.* 5:23-25 (1960)). In addition, it has been demonstrated that silicon was elevated in the aorta with focal atherosclerosis, as well as in the atherosclerotic focus itself. (*Folia Morph* 25:353-356 (1977)). Further, it has been reported that with advancing age, the $SiO_2$ level of human peribronchial lymph glands gradually increases even in those who have no history of exposure to dust. (*J. Pathol.* 51:269-275 (1940)). Our own work, moreover, has demonstrated an increase of kidney silicon levels in normal rats with aging.

Although silicon is an essential trace element for human growth and is necessary for bone formation, silicon intoxication has been shown to cause various diseases. In addition to cases of acute toxicity, there is justifiable suspicion that the pathogenesis of some chronic diseases may be related to prolonged exposure to concentrations of toxins insufficient to produce conspicuous manifestations (*J. Chron. Dis.* 27:135-161 (1974)). For example, a substantial portion of patients with terminal renal failure have no clearly definable etiology of their renal disease. It may be speculated therefore that some renal disease may be associated with chronic exposure to certain toxins including silicon.

Much information is known about the toxic effects of silicon in the lung. Varying amounts of silica normally enter the respiratory tract across the lung barrier as silicic acid and are eventually eliminated. Prolonged inhalation and accumulation of fine particulate silica in the lung however, produces a pulmonary inflammatory response, granuloma formation and chronic fibrosis (silicosis) (*Prin Int. Med.* 9th Ed., Isselbacher et al. (eds), McGraw-Hill Book Co., N.Y. 1980). In silicosis, the injury seems to be related to both the crystal structure of the silicon and the host response. Workers in stone quarries, or in other industries where sand or other silicate dusts are prevalent, are prone to contract this disease.

It is commonly believed that ingested silicates are both inert and nonabsorbable, but there has long been a suspicion that silicates are nephrotoxic in humans (*Scot Med. J.* 27:10–17 (1982). In 1922, Gye and Purdy investigated the toxicity of parenterally administered colloidal silica in rabbits which resulted in interstitial nephritis, hepatic fibrosis and splenomegaly within a period of weeks to several months (*Br. J. Exo. Path* 3:75–85 (1922)). These findings were later confirmed by Schepers et al. (*AMA Arch. Industr. Hlth.* 15:599 (1957)). In 1970, Newberne and Wilson showed that oral administration of certain silicates produced significant renal tubular damage and chronic interstitial inflamation in dogs (*Proc. Nat. Acad. Sci.* 65:872–875 (1970)). And in 1982, Dobbie and Smith showed that oral ingestion of magnesium trisilicate resulted in renal damage in guinea pigs in four months (*Scot. Med. J.* 27:10 (1982)).

In humans, chronic exposure to silica has been associated with mild renal functional abnormalities and minor histologic changes in the kidneys. Bolton et al. reported four patients with a history of intense silica exposure and rapidly progressive renal failure, and concluded that silicon appeared to be responsible for the nephrotoxic changes (*Am. J. Med.* 71:823 (1981)). Silicon has also been shown to have a direct dose-dependent toxic effect on the kidney (*J. Pathol.* 103:35–40 (1970)), and silicon particles are cytotoxic, as shown by studies demonstrating damage to macrophages ingesting silicon (*Am. Rev. Respir. Dis.* 113:643–665 (1976)).

Since it is known that the principal organ of silicon elimination is the kidney, it is not surprising that an increase in plasma silicon levels (*Biomedicine* 33:228–230 (1980)), as well as an increase in certain tissue silicon levels have been reported in studies of patients suffering from chronic renal failure and in patients on hemodialysis. (*J. Chron Dis* 27:135 161 (1974)). The accumulation of increased quantities of silicon in renal failure results from its decreased renal clearance (*J. Chron. Dis.* 27:135–161 (1974)). The high serum silicon levels demonstrated in hemodialysis patients have been associated with osteitis fibrosa (*Xth Intl. Cong. of Nephr.*, June 26–31, 1987), and elevated cerebral spinal fluid (CSF) silicon levels have been observed in patients with chronic renal insufficiency where CSF silicon levels increased as renal function declined. (*Neurology:* 86–789 (1983)). It has been hypothesized therefore, that since silicon is nephrotoxic and accumulates in blood and body tissues of patients with renal failure, silicon may contribute to the steady progression of renal failure once initiated. (Id)

In addition to silicon, aluminum has been found to accumulate in advanced kidney disease patients on chronic hemodialysis. Currently, the most effective means of increased removal of aluminum during hemodialysis, is by chelation with desferrioxamine (DFO). (*Clin. Nephr.* 24:594–597 (1985)). At the end of a dialysis treatment, the chelator is administered to the patient, whereupon at the next dialysis session, the aluminum-DFO complex is removed. Various dialysis related modalities may be used to remove the aluminum-DFO complex including hemodialysis, peritoneal dialysis, hemofiltration or charcoal (or resin) hemoperfusion. (*Kid. Int.* 33 suppl. 24:5–171 (1988)). Known side effects of DFO treatment include anaphylactic reactions, abdominal pain, posterior cataracts, visual impairments and predisposition to development of fungal infections. In addition, DFO has not yet been investigated for its ability to form stable complexes with silicon (*Clin. Neph.* 24 at Table 1 p. 595). A need continues to exist therefore, for a chelator that would help promote the removal of silicon accumulation in patients with advanced kidney disease on chronic hemodialysis.

Silicon may also be a neurotoxin. Silicon, together with aluminum, are significantly elevated in Alzheimer's disease in the neurofibrillary tangles, and in senile dementia there is a diffuse increase in silicon levels in the brain (*Science* 208:97–298 (1980)). Nikaido et al. demonstrated that patients with Alzheimer's disease showed a substantial increase of silicon in the cores and rims of the senile plaques. (*Arch. Neurol.* 27:549–554 (1922)).

Meso-2,3-Dimercaptosuccinic acid (DMSA) is a water soluble compound analogous to 2,3-dimercaptopropanol (BAL). In contrast to BAL however, DMSA is less toxic, has greater water solubility, limited lipid solubility, and is effective when given orally (*Fund. Appl. Tox* 11:715–722 (1988)).

DMSA is available as a white crystalline powder and exists in two forms, the meso form and the DL form. Because Meso-DMSA is easier to synthesize and purify, it is more readily available, and has been used in most published investigations. Meso-DMSA (m.p. 210°–211° C.) is sparingly soluble and must be titrated to approximately pH 5.5 to go into solution, or disolved in 5% $NaHCO_3$. The DL form (m.p. 124–125) on the other hand, is readily soluble in distilled water. (*Ann. Rev. Pharmacol. Toxicol* 23:193–215 (1983)). DMSA is available from a variety of biochemical specialty firms.

DMSA was originally introduced by Friedheim and DaSilva in 1954 to promote uptake of antimony during schistosomiasis therapy (*J. Pharm. Exo. Therap.* 246:84 (1988)), and was first recognized as an antidote for heavy metal toxicity by Liang et al. in 1957 (*Acta Physiol. Sin.* 21:24–32 (1957)). Since then, DMSA has been shown to remove toxic forms of lead, mercury and arsenic from the body via urinary excretion, presumably by forming water-soluble metal complexes or chelates (*Anal. Biochem.* 160:217–226 (1987)).

DMSA has been shown to have variable success as an antidote for other toxicities. DMSA was reported to be effective at reducing the concentration of aluminum in the liver, spleen and kidney (*Res. Com. Chem. Pathol. Pharm.* 53:93–104 (1986)), reducing the concentration of cobalt in the liver, brain, heart and blood (*Arch. Toxicol.* 58:278–281 (1986)), and as an antagonist for acute oral cadmium chloride intoxication by increasing the urinary elimination of cadmium (*Tox Appl. Pharm.* 66:361–367 (1982)). DMSA however, did not increase urinary and fecal excretion of cobalt (*Arch. Toxicol.* 58:278–281 (1986)), and showed lower efficacy than other chelating agents as an antidote for zinc poisoning (*Arch. Toxicol.* 61:321-323 (1988)). (See *Ann. Rev. Pharm. Toxicol.* 23:193-215 (1983) for a review of the success and failure of DMSA in treating toxicities).

DMSA has also been labeled with $^{99}$Tc for use in renal scanning (*J. Nucl. Med.* 16:28-32 (1973), tumor detection (*Clin. Otalary* 12:405-411 (1987); *Clin. Nucl. Med.* 13:159-165 (1988)) and for imaging myocardial infarcts (*Clin. Nucl. Med.* 12:514-518 (1987)).

DMSA has been reported as an effective and relatively nontoxic agent for treatment of metal poisoning. Other chelating agents have also been used as antidotes for metal toxicities, but these drugs have been shown to have many side effects. BAL is administered by a painful intramuscular injection and can cause nausea, vomiting and severe headache. Calcium disodium ethylenediaminetetraacetic acid (CaNa$_2$ EDTA) must be administered parenterally, either intravenously or intramuscularly. It is painful when given intramuscularly and when given in excessive dosage, can cause nephrotoxicity. Penicillamine is administered orally but is not as effective as BAL or CaNa$_2$ EDTA. Additionally, it can cause reactions resembling penicillin sensitivity, is potentially nephrotoxic and causes neutropenia (*Clinical Tox.* 25:39-51 (1987).

To date, there are no known chelating agents effective for silicon removal, as well as no previously demonstrated effects of silicon removal. A need exists therefore, for a method to remove silicon from the body, thereby improving blood pressure and kidney function, reducing neurological toxicities, and returning silicon to youthful levels.

SUMMARY OF THE INVENTION

Human exposure to silicon compounds is widespread, either in food, beverages, drinking water, medicine or the external environment. Many foods and beverages contain naturally occuring plant silicates, and there is an increasing use of silicon compounds in the food manufacturing industries where they are extremely useful in preparation and stabilization. Amorphous silicates are widely used as anticaking agents in manufactured food powders, extracts and condiments. Silicon is present in beverages largely due to the natural silicate content of the materials used in their production, as is the case with some beers made from grains. Silicates are frequently incorporated into medicines such as analgesic powders, mixtures and tablets. Collodial silicas are used in the pharmaceutical industry as desiccants since they have a large surface area and highly polar silanol surface favorable for water vapor absorption. Silicon present in silicate dusts or sand, and silicon used in the computer industry in semiconducting devices, represent yet other sources of silicon exposure.

Long term silicon ingestion and accumulation, as well as silicon intoxication from industrial sources, creates the potential for nephrotoxicity, neurotoxicity and other disease states. In addition, increased silicon levels in cases of renal failure or hemodialysis may further aggravate these conditions. Since silicon is a known component of scar tissue, elevated silicon levels could contribute to progressive scarring.

Thus, it is the object of the present invention to provide a method of reducing silicon levels in the body.

It is the second object of the invention to provide a method of removing kidney silicon in various types of kidney diseases, thereby retarding progressive renal scarring and failure.

It is another object of the present invention to provide a method of removing accumulated silicon thereby improving blood pressure and returning kidney function to normal levels.

It is another object of the present invention to provide a method for treating accumulation of silicon in advanced kidney disease.

It is yet a further object of the present invention to provide a method of removing brain silicon levels thereby preventing the onset of dementia and Alzheimer's Disease or improving a current diseased status.

DETAILED DESCRIPTION

Figure 1:
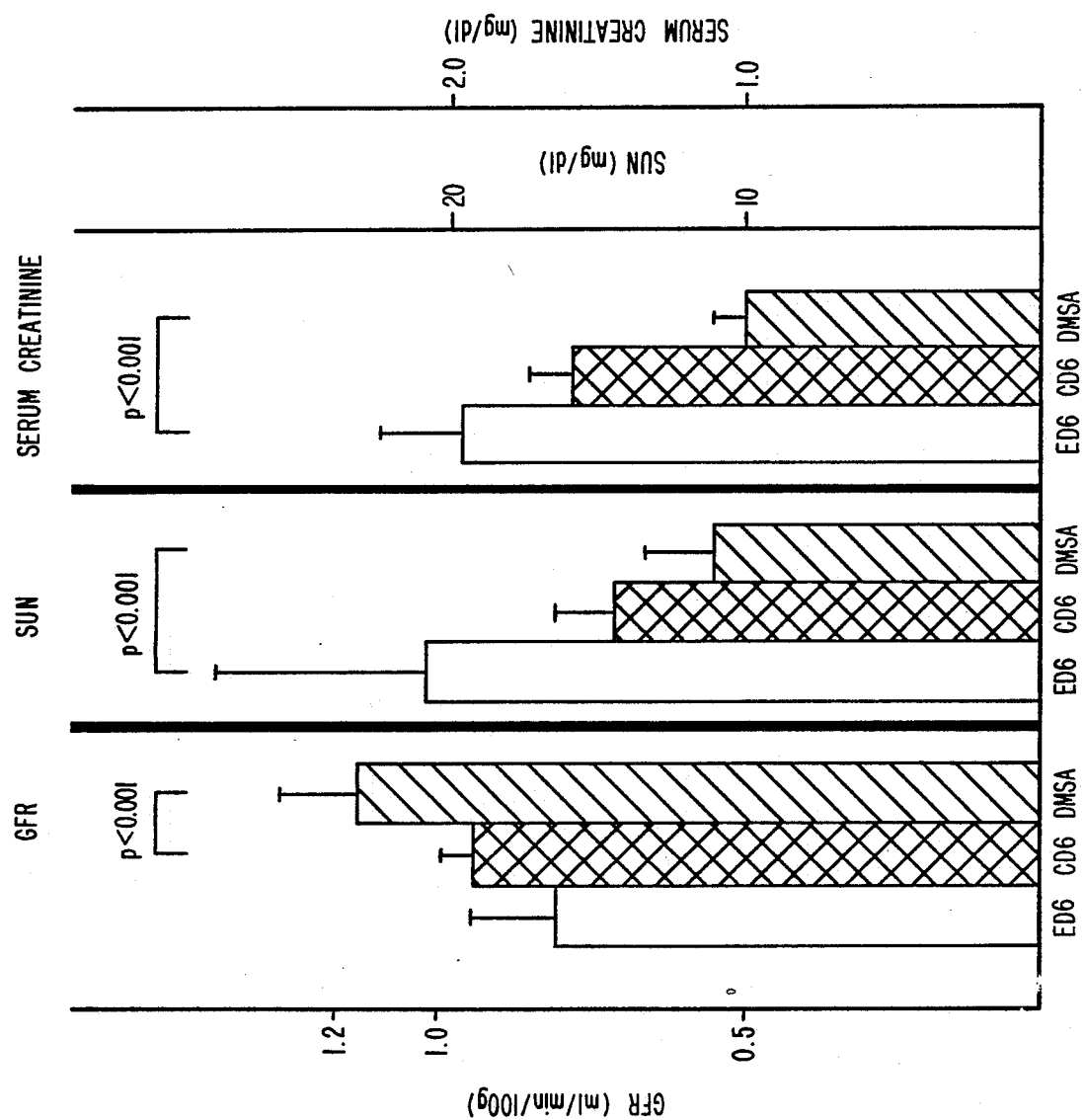
FIG. 1 is a graph showing the effect of DMSA on the Glomerular Filtration Rate (GFR). The DMSA group is compared to normal controls (CD6) and to animals treated with lead for six months, then sacrificed at twelve months (ED6).

In the course of an experiment designed to examine the effect of lead on kidney function and blood pressure, as well as the effect of DMSA on removal of lead, we have unexpectedly found that DMSA reduces kidney silicon to levels seen in young normal control animals and far below the aged normal controls. In addition, DMSA-treated animals had restoration of glomerular filtration rates (GFR) and blood pressure to the same level as young animals due to reduction in silicon. Although DMSA also reduced kidney lead content, the reduction in lead was less than that seen in lead-treated animals where lead was discontinued at six months (ED6) and where no improvement in GFR or blood pressure was seen. Thus the reduction in silicon levels was more likely to be related to these favorable effects than reduction in lead.

EXAMPLE 1

Rat-Kidney Emission Spectroscopy Results

Male Sprague-Dawley rats were fed beginning at eight weeks of age and sacrificed according to the following schedule:
(1) Controls (C): fed only a semi-purified diet
   C1—sacrificed at one month after initiation of the experiment
   C6—sacrificed at six months
   C12 sacrificed at twelve months
   CD6—sacrificed at 12 months
(2) Experimental continuous (EC): fed semi-purified diet and 0.5% lead acetate in drinking water throughout the experiment.
   EC1—sacrificed at one month
   EC12—sacrificed at twelve months
(3) ED6—Experimental discontinuous: fed semipurified diet and 0.5% lead acetate in drinking water for six months, no lead in drinking water for the subsequent months sacrificed at twelve months.

(4) DMSA: fed semi-purified diet and 0.5% lead acetate in drinking water for six months, no lead for the subsequent six months while treated with 0.5% DMSA in drinking water for five days every two months; sacrificed at twelve months.

After sacrifice, kidneys were excised, digested, and analyzed using an emission spectrometer procedure known in the art for determining elements frequently found in biological tissues. Specifically, in this study, the sample elements were volatilized and excited in a a D.C. arc. The various element signals were sorted and recorded with an ARL 1.5 m grating spectrometer. The signal data, which were automatically transferred to IBM punched cards, were processed to concentrations in ppm dry weight with an IBM 360-91 computer. The following elements were determined: sodium, potassium, calcium, phosphorus, magnesium, cadmium, zinc, copper, lead, iron, manganese, aluminum, silicon, boron, tin, cobalt, nickel, molybedenum, titanium, chromium, strontium, barium, lithium, silver and vanadium. Results are as shown in Table 1. Only silicon and lead are listed as the other elements did not show major changes.

As can be seen in Table 1, C12 and CD6 silicon levels increased significantly with age when compared to C1 and C6. The rats fed DMSA however, showed significantly decreased levels of silicon as compared to the older controls (C12 and CD6) and to experimental animals (EC12 and ED6).

in Table 2, and FIG. 1. FIG. 1 shows the effect of DMSA treatment on GFR. The DMSA group is compared to normal controls (CD6) and to animals treated with lead for six months, then sacrificed at twelve months (ED6). As can be seen in FIG. 1, animals given DMSA showed significantly increased GFR, confirmed by lower SUN and serum creatinine levels than those in the animals without DMSA.

EXAMPLE 3

Blood Pressure Levels

Figure 2:
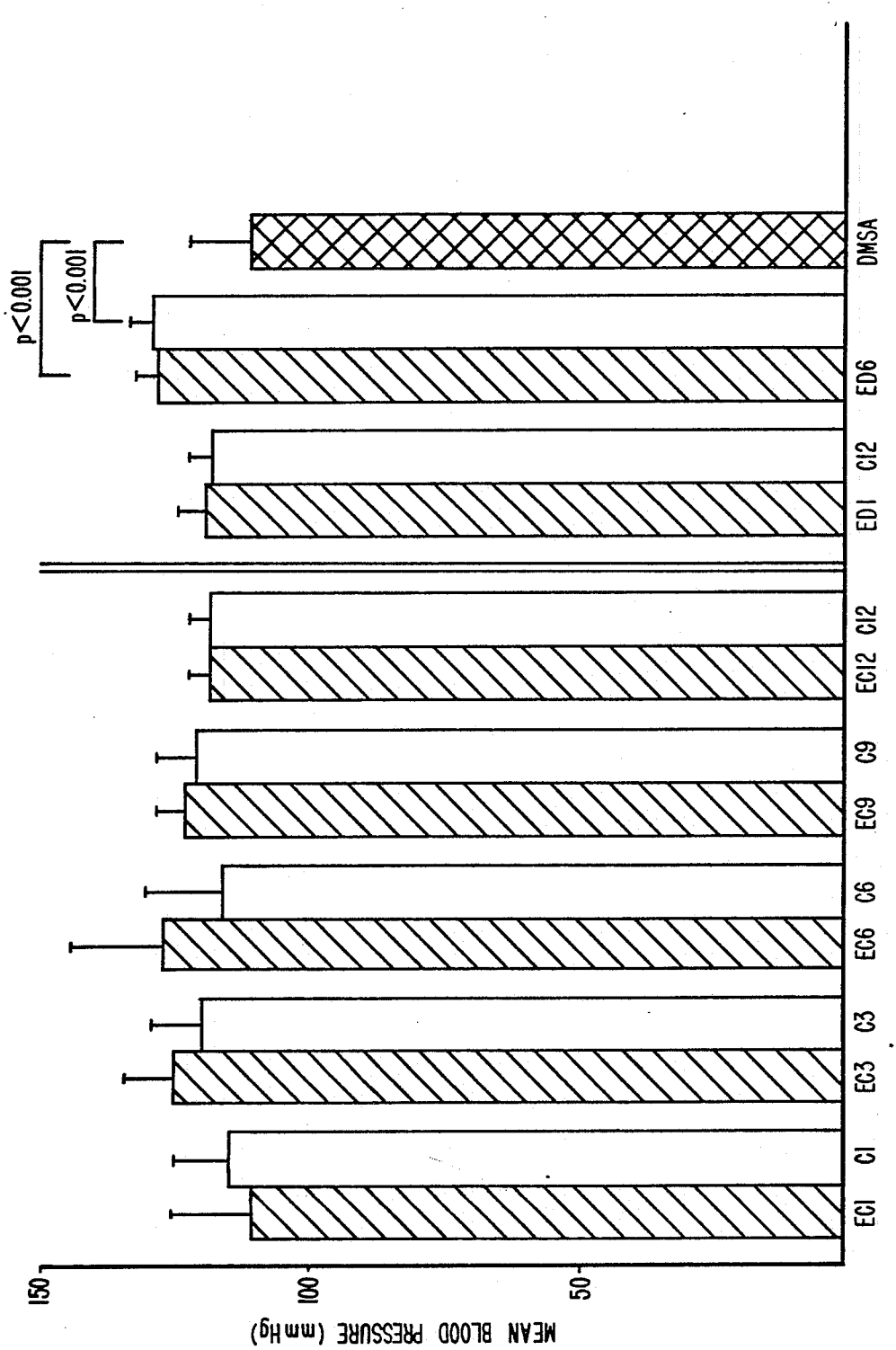
FIG. 2 is a graph showing the effect of DMSA on mean blood pressure.

Mean blood pressure recordings were obtained using an automated tail blood pressure device. Results are shown in FIG. 2. Blood pressure is shown to increase with age in both control animals and lead treated animals. DMSA treatment restored blood pressure to levels seen in young animals (C1) and significantly reduces blood pressure below ED6 and CD6 controls.

By providing a method according to the above invention, several beneficial effects will be realized. First, reduction of silicon levels in the blood and tissue will reduce blood pressure and improve kidney function. Second, reduction of silicon by this method will prevent or retard the progression of chronic renal failure. Furthermore, removal of silicon will prevent the onset, or improve the current status of dementia and Alzheimer's Disease.

Other and further embodiments of the invention are readily apparent from the above description of the invention, and these embodiments are believed to be within the scope of the invention.

TABLE 1

| Elements | TRACE ELEMENTS IN KIDNEY | | | | | | | |
|---|---|---|---|---|---|---|---|---|
| | C1 | C6 | C12 | CD6 | EC1 | EC12 | ED6 | DMSA |
| Si (ppm) | 9.42± 8.64 | 12.32± 6.05 | 98.00± 38.74 | 299.00± 209.74 | 8.31± 14.10 | 137.00± 98.01 | 124.22± 118.89 | 5.31±[a] 8.08 |
| Pb (ppm) | 5.00± 2.96 | 1.97± 1.53 | 1.57± 1.46 | 0.75± 1.39 | 70.33± 23.67 | 291.78± 187.18 | 54.22± 24.94 | 132.29± 127.96 |

EC1 = experimental group (fed 0.5% lead in drinking water); sacrificed at 1 month.
C1 = controls for EC1.
C6 = controls sacrificed at 6 months.
EC12 = experimental group (fed 0.5% lead in drinking water); sacrificed at 12 months.
C12 = controls for EC12.
ED6 = experimental discontinuous group (fed 0.5% lead in drinking water for 6 months, no lead for the subsequent 6 months); sacrificed at 12 months.
CD6 = controls for EDG.
DMSA = DMSA-treated rats (fed 0.5% lead in drinking water for 6 months, no lead for the subsequent 6 months while treated with 0.5% DMSA in drinking water for 5 days every 2 months); sacrificed at 12 months.

EXAMPLE 2

Determination of GFR

Measurement of the glomerular filtration rate (GFR) provides a sensitive and commonly employed index of overall renal excretory function. GFR can be assessed indirectly by measurement of plasma creatinine or serum urea nitrogen levels, and directly by clearance of insulin ($C_{36}H_{62}O_{31}$) or by clearance of various radioactive substances handled by the kidney in the same way as inulin (i.e. iothalamate-$I^{125}$). When renal excretory function is impaired, either acutely or chronically, one or more of the GFR determinants is altered unfavorably so that total GFR declines. In this study GFR was measured by blood turnover rate of Iothalamate $I^{125}$ (*J. Lab Clin. Med.*, 89:845-856 (1972)), as well as by plasma creatinine and serum urea nitrogen. Results are shown

TABLE 2

| | GFR (ml/min/100 g) | SERUM CREAT. (mg/dl) | SUN (mg/dl) |
|---|---|---|---|
| C1 | 0.59± 0.27 | 0.46± 0.04 | 19.3± 4.0 |
| C6 | 1.09± 0.13 | 1.08± 0.14 | 12.8± 2.4 |
| CD6 | 0.96± 0.05 | 1.59± 0.14 | 14.4± 2.0 |
| ED6 | 0.82±** 0.14 | 1.96±** 0.28 | 20.8± 7.2 |
| DMSA | 1.16±* 0.13 | 1.00±* * 0.10 | 11.1±* 2.2 |

*P <0.05 when compared to ED6 and CD6
**P <0.05 when compared to CD6

We claim:

1. A method of reducing silicon levels in the blood of a human or other animal requiring such treatment, comprising administering to said human or animal an effective amount of Dimercaptosuccinic Acid.

2. A method according to claim 1 wherein administration is oral or parenteral.

3. A method of reducing silicon levels in the tissue of a human or other animal requiring such treatment, comprising administering to said human or animal an effective amount of Dimercaptosuccinic Acid.

4. A method according to claim 1 wherein administration is oral or parenteral.

5. A method of reducing silicon levels in human tissue comprising orally administering to said human an effective amount of Dimercaptosuccinic Acid.

6. A method of reducing silicon levels in human blood comprising orally administering to said human an effective amount of Dimercaptosuccinic Acid.

7. A method for reducing blood pressure comprising administering dimercaptosuccinic acid in an amount effective to reduce silicon levels in the body.

8. A method for treating chronic renal failure comprising administering dimercaptosuccinic acid in an amount effective to reduce silicon levels in the body.

9. A method for treating Alzheimer's disease comprising administering dimercaptosuccinic acid in an amount effective to reduce silicon levels in the body.

10. A method for treating senile dementia comprising administering dimercaptosuccinic acid in an amount effective to reduce silicon levels in the body.

11. A method for improving renal function comprising administering dimercaptosuccinic acid in an amount effective to reduce silicon levels in the body.

12. A method for treating accumulation of silicon in advanced kidney disease comprising:
   a. administering dimercaptosuccinic acid (DMSA) in an amount effective to remove silicon; and
   b. removing the Silicon-DMSA complex (from the blood) by a dialysis related modality.

13. A method according to claim 12 wherein administration is oral or parenteral.

14. A method according to claim 12 wherein the dialysis related modality is hemodialysis, peritoneal dialysis, hemofiltration or charcoal (or resin) hemoperfusion.

* * * * *